(12) United States Patent
Utermoehlen et al.

(10) Patent No.: US 10,751,477 B2
(45) Date of Patent: Aug. 25, 2020

(54) DETERMINING DEVICE FOR DETERMINING A VALUE REPRESENTING A DOSE OF A DOSE METERING DEVICE, AND A METHOD FOR OPERATING SAME

(71) Applicant: Robert Bosch GmbH, Stuttgart (DE)

(72) Inventors: Fabian Utermoehlen, Leonberg (DE); Andreas Merz, Freiberg am Neckar (DE); Stefan Leidich, Rutesheim (DE)

(73) Assignee: Robert Bosch GmbH, Stuttgart (DE)

( * ) Notice: Subject to any disclaimer, the term of this patent is extended or adjusted under 35 U.S.C. 154(b) by 165 days.

(21) Appl. No.: 16/083,427

(22) PCT Filed: Mar. 8, 2017

(86) PCT No.: PCT/EP2017/055495
§ 371 (c)(1),
(2) Date: Sep. 7, 2018

(87) PCT Pub. No.: WO2017/153501
PCT Pub. Date: Sep. 14, 2017

(65) Prior Publication Data
US 2019/0091411 A1 Mar. 28, 2019

(30) Foreign Application Priority Data
Mar. 10, 2016 (DE) .................. 10 2016 203 905

(51) Int. Cl.
*A61M 5/31* (2006.01)
*A61M 5/315* (2006.01)
(Continued)

(52) U.S. Cl.
CPC ........ *A61M 5/31585* (2013.01); *A61M 5/178* (2013.01); *G01D 5/202* (2013.01);
(Continued)

(58) Field of Classification Search
CPC .............. A61M 5/31585; A61M 5/178; A61M 2205/3317; A61M 2205/3561; A61M 2205/502; G01D 5/202
See application file for complete search history.

(56) References Cited

U.S. PATENT DOCUMENTS

2009/0076460 A1* 3/2009 Nielsen ............. A61M 5/31525
604/207

FOREIGN PATENT DOCUMENTS

DE    42 11 614 A1    10/1993
DE    100 14 979 A1    4/2001
(Continued)

OTHER PUBLICATIONS

International Search Report corresponding to PCT Application No. PCT/EP2017/055495, dated Jun. 9, 2017 (German and English language document) (7 pages).

*Primary Examiner* — Amber R Stiles
(74) *Attorney, Agent, or Firm* — Maginot, Moore & Beck LLP

(57) ABSTRACT

A determination device for determining a value representing a dose of a dose metering device includes an eddy-current-based rotational angle sensor. The rotational angle sensor can be coupled to a rotatable dosing knob of the dose metering device and can image a rotational angle of the dosing knob representing the dose in a rotational angle signal. The determination device further includes an analysis device that can establish the value of the dose using the rotational angle signal.

17 Claims, 5 Drawing Sheets

(51) Int. Cl.
*G01D 5/20* (2006.01)
*A61M 5/178* (2006.01)
(52) U.S. Cl.
CPC ............... *A61M 2205/3317* (2013.01); *A61M 2205/3561* (2013.01); *A61M 2205/502* (2013.01)

(56) References Cited

FOREIGN PATENT DOCUMENTS

| | | |
|---|---|---|
| DE | 10 2006 006 784 A1 | 8/2007 |
| EP | 0 530 090 A1 | 3/1993 |
| WO | 92/14121 | 8/1992 |
| WO | 2013/120778 A1 | 8/2013 |
| WO | 2014/064691 A2 | 5/2014 |
| WO | 2015/074979 A2 | 5/2015 |

* cited by examiner

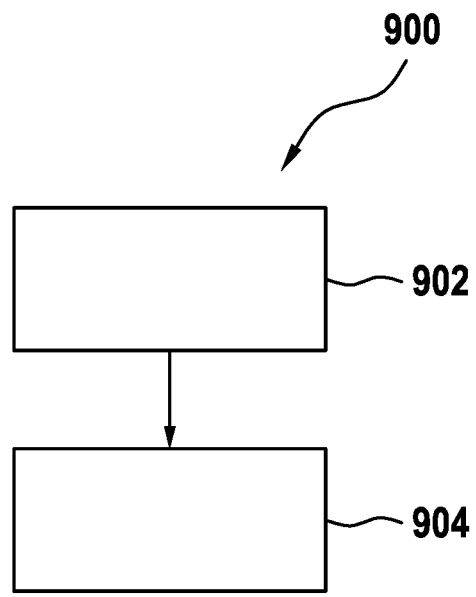

DETERMINING DEVICE FOR DETERMINING A VALUE REPRESENTING A DOSE OF A DOSE METERING DEVICE, AND A METHOD FOR OPERATING SAME

This application is a 35 U.S.C. § 371 National Stage Application of PCT/EP2017/055495, filed on Mar. 8, 2017, which claims the benefit of priority to Serial No. DE 10 2016 203 905.9, filed on Mar. 10, 2016 in Germany, the disclosures of which are incorporated herein by reference in their entirety.

BACKGROUND

The disclosure is directed to a device or a method according to the generic definition as disclosed. The subject matter of the disclosure is also a computer program.

For the treatment of illnesses, for example, diabetes mellitus, a patient can independently inject a medication, for example, insulin. For this purpose, the patient can use an injection device which enables a preselection of the dose to be dispensed.

WO 2015/074979 A2 discloses a spring-assisted medication dispensing device.

SUMMARY

Against this background, the approach proposed here proposes a determining device for determining a value representing a dose of a dose metering device, a dose metering device, furthermore a method for operating a determining device, and finally a corresponding computer program as disclosed. Advantageous refinements and improvements of the device are possible by way of the measures as disclosed.

The dose to be dispensed can be set via a rotary knob on the device. The dispensing of the dose can be started by pressing the rotary knob. The dose is proportional to a rotational angle between a first angle position of the rotary knob before beginning the setting and a second angle position after the end of the setting. Therefore, an inference about the dose can be drawn by determining the rotational angle.

In the approach proposed here, the rotational angle is determined via an eddy-current-based rotational angle sensor. This sensor is robust, contactless, and can image the rotational angle with high accuracy.

A determining device for determining a value representing a dose of a dose metering device is proposed, wherein the determining device has the following features:

an eddy-current-based rotational angle sensor, which can be coupled to a rotatable dosing knob of the dose metering device and is designed for the purpose of imaging a rotational angle of the dosing knob representing the dose in a rotational angle signal; and an analysis device, which is designed for the purpose of determining the value of the dose using the rotational angle signal.

A dose metering device can be understood as a medication dispensing device, in particular an insulin injection device. A dose can be a fluid quantity or a liquid volume, for example, a liquid medication such as insulin, which is to be dispensed or will be dispensed by the dose metering device. A dosing knob can be an operating element of the dose metering device. The dosing knob can furthermore be able to be pressed. The rotational angle can be an angle step between a starting position and an end position of the dosing knob. A rotational angle signal can be an electrical signal.

The rotational angle sensor can have a coil unit and an electrically conductive interference surface unit, which is spaced apart in relation thereto and is arranged so it is rotatable. A coil unit can comprise at least one electrical coil. An interference surface unit can comprise at least one electrically conductive interference surface. The coil unit can be a component to which current can be applied. The interference surface unit can be a passive component without electrical connection. The coil unit can be connected to an electrical circuit for providing the rotational angle signal. The electrical circuit can provide an electrical signal for the coil unit which forms one electromagnetic alternating field per coil. The alternating field is influenced by the interference surface. Depending on a relative position between the coil and the interference surface, a position-dependent inductance of the coil results. The inductance can be analyzed in the electrical circuit and an inference can be drawn about the relative position.

The coil unit can have a number of coils, which differs from a number of interference surfaces of the interference surface unit. In particular, the number of the coils can be greater than the number of the interference surfaces of the interference surface unit. Due to the different numbers, signal curves which have a phase offset result at the coils. The phase offset enables an unambiguous determination of the present angle position and/or the rotational direction.

The interference surface unit can have at least two interference surfaces. The coil unit can have at least three coils. Three coils enable three signals which can be analyzed. In the case of three signals, a redundancy optionally results, since the angle position can also be ascertained from two signals, depending on the coil design and interconnection.

The coils of the coil unit can be formed as conductor tracks on a printed circuit board aligned orthogonally to an axis of rotation of the dosing knob. Conductor tracks can be introduced easily into printed circuit boards. A shape of the conductor tracks can be freely selected.

The determination device can have a display device, which is designed for the purpose of displaying the value or a parameter representing the value. The display device can be referred to as a display screen. The display device can display the value, a parameter representing the value, and/or other items of information. The dose can easily be read off by way of the display device.

The determination device can have a communication device, which is designed for the purpose of providing the value or a parameter representing the value. A communication device can be designed for the purpose of establishing a wireless connection to an analysis device. Monitoring of a number of doses can be carried out over a longer period of time by way of the communication.

The rotational angle sensor can be designed for the purpose of providing a dispensing signal upon dispensing of the dose. In addition to the rotational angle, a linear movement can thus also be determined upon the triggering of the dispensing. For example, the rotational angle sensor can comprise a switch which provides the dispensing signal in response to the linear movement. A change of a distance between the coil unit and the interference surface unit can also be determined by the linear movement and imaged in the dispensing signal.

Furthermore, a dose metering device having the following features is proposed:

a dosing knob for setting a dose, wherein the dose is settable via a rotational angle of the dosing knob; and a determining device according to the approach proposed here, wherein the rotational angle sensor is coupled to the dosing knob to determine the rotational angle.

The analysis device can be arranged in the dosing knob. A previously unused space can thus be used and the external form of the dose metering device remains unchanged.

Furthermore, a method for operating a determining device for determining a dose of a dose metering device is proposed, wherein the method has the following steps:

reading in a rotational angle signal of an eddy-current-based rotational angle sensor, which is coupled to a rotatable dosing knob of the dose metering device, of the determination device, wherein the rotational angle signal images a rotational angle of the dosing knob representing the dose; and establishing a value of the dose using the rotational angle signal.

An AC voltage can be applied to the rotational angle sensor to establish the rotational angle signal. An electromagnetic alternating field can be built up at least one coil by the AC voltage. An inductance of the coil can be analyzed to obtain the rotational angle signal.

A collective value can be established using values representing a plurality of doses. The collective value can, for example, represent a total dose within a predetermined period of time. A dosed daily dose can thus be established, for example.

This method can be implemented, for example, in software or hardware or in a mixed form of software and hardware, for example, in a control unit.

A computer program product or computer program having program code which can be stored on a machine-readable carrier or storage medium such as a semiconductor memory, a hard drive memory, or an optical memory and is used for carrying out, implementing, and/or controlling the steps of the method according to any one of the above-described embodiments is also advantageous, in particular if the program product or program is executed on a computer or a device.

Exemplary embodiments of the approach proposed here are illustrated in the drawings and explained in greater detail in the following description. In the figures:

BRIEF DESCRIPTION OF THE DRAWINGS

FIG. 9 shows a flow chart of a method for operating a determination device according to one exemplary embodiment.

DETAILED DESCRIPTION

In the following description of advantageous exemplary embodiments of the disclosure, identical or similar reference signs are used for the similarly acting elements illustrated in the various figures, wherein a repeated description of these elements is omitted.

Figure 1:
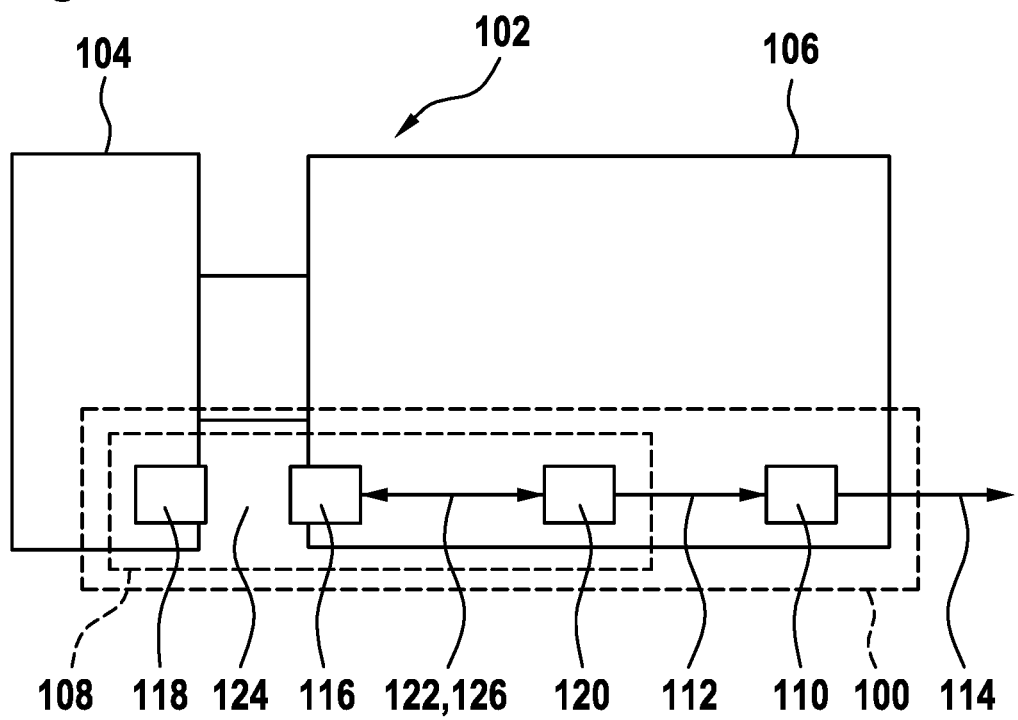
FIG. 1 shows a block diagram of a determination device according to one exemplary embodiment.

FIG. 1 shows a block diagram of a determination device 100 according to one exemplary embodiment. The determination device 100 is part of a dose metering device 102 having a dosing knob 104 for setting a dose to be dispensed. The dosing knob 104 is rotatable in relation to a handle 106 of the dose metering device 102. The dose is settable via a rotational angle of the dosing knob 104 in relation to the handle 106. The dose metering device 102 can be, for example, a medication dispensing device, such as an insulin pen. The quantity to be dispensed or individual dose, respectively, of the medication or insulin, respectively, can then be set via the dosing knob 104.

For example, the dosing knob 104 is coupled to a thread inside the handle 106, via which a stroke of a piston is preset by rotating the dosing knob 104. The stroke determines the dose. The stroke can be triggered by an axial press on the dosing knob, in order to dose the fluid.

The determination device 100 is designed for the purpose of determining a value representing the dose. For this purpose, the determination device 100 has an eddy-current-based rotational angle sensor 108 coupled to the dosing knob 104 and an analysis device 110. The rotational angle sensor 108 provides a rotational angle signal 112 imaging the rotational angle. The analysis device 110 determines the value 114 of the dose using the rotational angle signal 112.

The rotational angle sensor 108 has a coil unit 116 and an interference surface unit 118. The coil unit 116 is connected here to the handle 106. The interference surface unit 118 is arranged spaced apart in relation thereto and is connected to the dosing knob 104. The interference surface unit 118 rotates with the dosing knob 104 in relation to the coil unit 116. The interference surface unit 118 has at least one electrically conductive interference surface. The coil unit 116 has at least one electrically conductive coil. The coil unit 116 is connected to a sensor electronics unit 120 and an AC voltage 122 is applied to the coil unit by this electronics unit. An electromagnetic alternating field 124 is thus built up at the coil. If at least one interference surface of the interference surface unit 118 is arranged in an influence region of the alternating field 124, the alternating field 124 is influenced and an inductance 126 of the coil changes.

The coil is part of a resonant circuit of the sensor electronics unit 120. A resonance frequency of the resonant circuit is dependent on the inductance 126. To operate the resonant circuit in resonance, the sensor electronics unit 120 adapts a frequency of the AC voltage 122 to the resonance frequency. The frequency of the AC voltage 122 is thus dependent on the relative position of coil and interference surface. The relative position is dependent on the rotational angle. Since a geometry of the coil unit 116 and the interference surface unit 118 is known, the sensor electronics unit 120 can provide the rotational angle signal 112 using a relationship between the resonance frequency and the rotational angle.

In other words, the coil assembly 116 of the rotational angle sensor 108 is part of a resonant circuit assembly of the rotational angle sensor 108. The inductance 126 of coils of the coil assembly 116 is influenced by the interference surface assembly 118, which is arranged so it is rotatable in relation to the coil assembly 116, of the rotational angle sensor 108. The rotational angle signal 114 is determined using resonance frequencies, which are influenced by the inductance 126, of resonant circuits of the resonant circuit assembly.

The analysis device 110 reads in the rotational angle signal 112 and provides the value 114 of the dose using a relationship between the stroke of the piston and the rotational angle of the dosing knob 104.

An injection device 102, in particular an insulin pen 102, comprising a dosing sensor system 100 based on an eddy-current rotational angle sensor 108 is proposed.

The lack of endogenous insulin in the case of a diabetes mellitus disease can be treated by injection of an insulin preparation. The injection can be executed by disposable syringes, permanently provided insulin pumps, and also disposable and multiuse pens. An injection pen can be similar to a very thick ballpoint pen and is equipped with insulin cartridges. A cartridge is a cylindrical ampule, which has a pierce-through membrane on one side. The other side is closed using a displaceable plug.

The required insulin quantity is set by rotation using a dosing knob 104. In this case, the dosing knob 104 can also execute a translational movement in addition to the rotational movement. The greater the set angle is, the farther the dosing knob 104 is unscrewed from the housing 106 via a thread. The distance between dosing knob 104 and housing 106 then corresponds to the path length by which the insulin cartridge is emptied upon pressure on the dosing knob 104. The path length can be scaled using a transmission factor. For this purpose, a plunger presses on the cartridge. This plunger is arranged on the end of a further threaded rod, which may only be rotated in one direction via a locking mechanism. It is ensured by a further mechanical component or a driver that the dosing knob 104 can at most be unscrewed as far as the remaining fill level in the ampule.

The dosing knob 104 can also only execute a rotational movement. The dosing knob 104 can also be embodied as rotatable, wherein its distance to the housing 106 is not changed. A spring is tensioned by the rotation, for example, the potential energy of which is converted by a mechanism into a translational movement of the plunger during the injection.

In the insulin pen 102 proposed here, the last insulin dose with corresponding injection time is continuously determined.

An injection device 102, in particular an insulin pen 102, is provided by the approach proposed here, which contains an integrated rotational angle sensor 108 based on eddy current, via which the rotational angle of the dosing wheel 104 or dosing knob 104 and thus the injected insulin quantity can be determined. The injection device 102 comprises, in addition to the rotational angle sensor 108, a microcontroller 110 for measured data acquisition. Furthermore, the injection device 102 can have electronic components for communication with external devices, for example, a smart phone.

The core is a sensor assembly 100 for acquiring the presently injected insulin quantity in the form of a rotational angle sensor 108 based on eddy current, which determines the position of the dosing knob 104, via which the dose may be inferred. The value 114 is stored and displayed on an integrated display screen and/or transmitted to an external device.

An enhancement of the user safety thus results. A reduced management effort results due to the automatic determination of the insulin quantity, since manual logging can be omitted for the physician and instead the automatically determined dose value 114 is electronically documented in a smart phone app and can be electronically transmitted, for example. The external form of the insulin pen 102 can remain unchanged. Since already existing components can be used, the solution proposed here is cost-effective. Inductive signals can be precisely analyzed.

Figure 2:
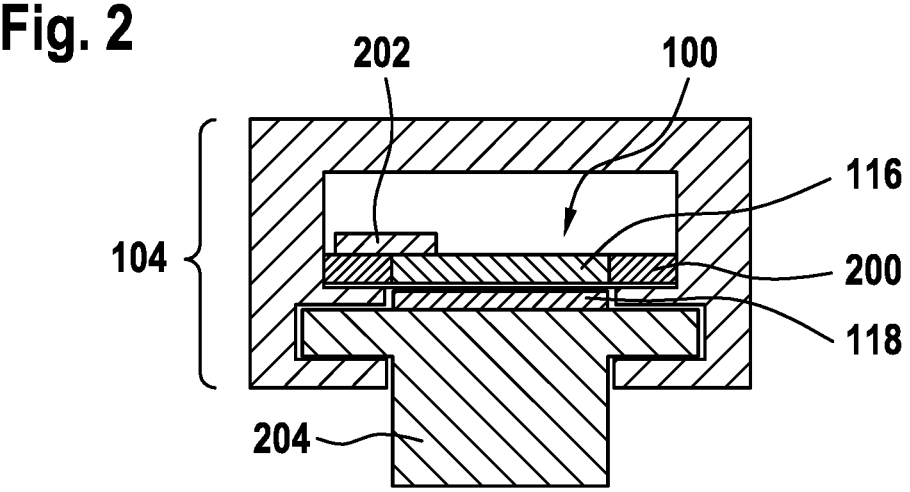
FIG. 2 shows a sectional illustration of a determination device according to one exemplary embodiment.

FIG. 2 shows a sectional illustration of a determination device 100 according to one exemplary embodiment. The determination device 100 substantially corresponds to the determination device in FIG. 1.

The determination device 100 is arranged here in the dosing knob 104. In this case, a printed circuit board 200 comprising the coil unit 116 is arranged in a cavity of the dosing knob 104. The analysis device 110 and the rotational angle sensor 108 are supplied with electrical energy via a button cell arranged in the dosing knob 104 or another energy accumulator (for example, capacitor) 202.

The interference surface unit 118 is connected to a part 204 of the dose metering device, on which the dosing knob 104 is supported so it is rotatable.

The integration in the injection pen is illustrated. All electronic components 100 for determining the inductance, for computing the dose, and for transmitting the data are arranged on a printed circuit board 200 inside the dosing knob 104. Alternatively, a housing in the housing is possible. However, this requires greater modifications in relation to the conventional design.

The printed circuit board 200 is schematically illustrated, which bears the sensor coils 116, the resonance capacitors for the preferred measurement of the inductance via the resonance frequency of a resonant circuit, a power supply 202, for example, a button cell, and further components. These comprise at least one microcontroller for measuring the resonance frequencies and for computing the dose and also a module for wireless transmission of the value, for example, via Bluetooth or NFC. The printed circuit board 200 is integrated into the dosing knob 104, which is supported so it is rotatable in relation to a stationary assembly 204 of the insulin pen. This assembly 204 bears the target structures 118. The distance between target 118 and sensor printed circuit board 200 can be kept constant via a spring (not shown).

The measurement of the rotation is the central task of the rotational angle sensor 100. In one exemplary embodiment, the activation of the insulin pen or the initiation of the injection, respectively, is discriminated by pressing the dosing knob 104. The activation is detectable by integration of a spring between the dosing knob 104 and the stationary assembly 204. By the pre-tension, for example, with a Newton [N], the spring effectuates a defined distance between the sensor coils 116 on the printed circuit board 200 and the target elements 118 on the stationary assembly 204. The pre-tension can be overcome by applying a force exceeding the pre-tension in the longitudinal direction. The distance between sensor coil 116 and target 118 is accordingly reduced. The reduction of the distance causes an elevation of the frequency shift of the resonant circuits. For example, the upper value of a, for example, three-phase sinusoidal system is elevated to 32 MHz instead of 29 MHz. After application of the Clarke transformation, an ideally offset-free sine/cosine system results. The distance between the sensor coils 116 and the target 118 can be concluded by computation of the amplitude via $a=\sin^2+\cos^2$. Alternatively, a contact switch in the dosing knob 106 is also possible, which is closed by the pressure of the user during the injection.

Figure 3:
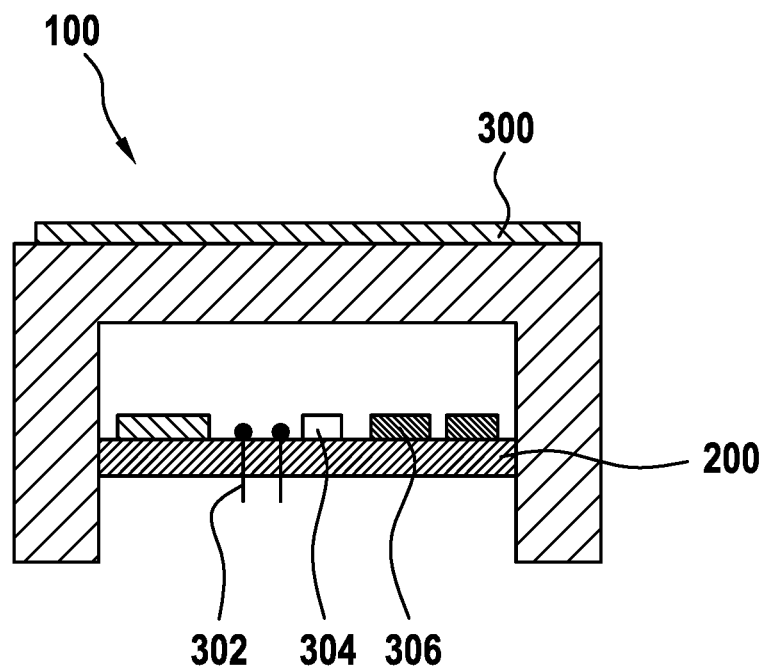
FIG. 3 shows a sectional illustration of a determination device having a display device according to one exemplary embodiment.

FIG. 3 shows a sectional illustration of a determination device 100 comprising a display device 300 according to one exemplary embodiment. The determination device 100 is arranged inside the dosing knob 104 as in FIG. 2. The display device 300 is arranged on an outer side of the dosing knob 104. In addition, discrete components are arranged here on the printed circuit board 200. In addition to through contacts 302 to the coil unit (not shown), a capacitor 304 is arranged as part of a resonant circuit. In addition, electronic components 306 comprising integrated circuits are arranged for measuring the frequency of the resonant circuit.

Alternatively or additionally to the wireless transmission, the value of the dose can also be displayed on a display screen 300 after the computation from the rotational angle. This display screen can be located on the upper side of the dosing knob 104. In one exemplary embodiment, an electronic ink display screen 300 is used, which enables a very low-energy continuous display.

In one exemplary embodiment, a determination of the time is part of the microcontroller and can be initialized, for example, upon a first radio contact. Furthermore, a capacitor 304 is part of the resonant circuit comprising the two coil contacts 302. The electronic components 306 are designed for measuring the frequency, for computing the rotational angle and the dose, and for wireless communication. All components are integrated on a printed circuit board 200.

Figure 4:
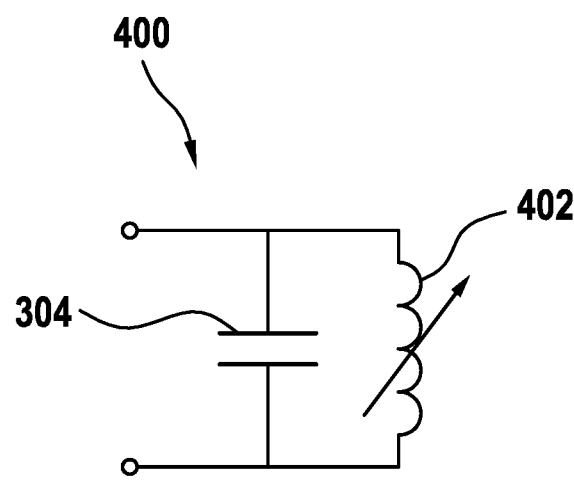
FIG. 4 shows an illustration of a resonant circuit according to one exemplary embodiment.

FIG. 4 shows an illustration of a resonant circuit 400 according to one exemplary embodiment. The resonant circuit 400 substantially corresponds to one of the resonant circuits in FIG. 3. The resonant circuit has a variable inductance 402 or a coil 402 having variable inductance and a capacitor 304 connected in parallel thereto. The inductance 402 corresponds to one of the coils of a coil unit, as are shown in FIGS. 1 and 2. The inductance 402 is influenced by the position of the interference surfaces of the interference surface unit.

The fundamental measuring effect of the rotational angle sensor is the inductance change of a planar coil 402 when a target made of electrically conductive material is located above it. If an AC voltage is applied to the coil 402, an electromagnetic alternating field thus results, which induces an eddy current in the target. This generates a field opposing the first field, which results in a reduced inductance of the sensor coil 402. If the coil 402 is interconnected in an electrical resonant circuit 400, the resonance frequency thereof thus changes according to $$f_0 = \frac{1}{2\pi\sqrt{L \cdot C}}.$$

The more the sensor coil 402 is covered by the target or the closer the target comes to the sensor coil 402, the greater the frequency of the resonant circuit 400 thus becomes. At constant distance between sensor coil 402 and target, a frequency change results due to scanning of the sensor coil 402 by the target. For this purpose, the target is structured along its circumference. A measurement of the frequency, for example, by counting the periods within a defined time window, accordingly enables an inference of the target position. The overall assembly is thus suitable as a rotational angle sensor. The capacitors 304 used are selected in such a way that a frequency in the range of several tens of megahertz is achieved.

In principle, various embodiments of the coils 402 and the target are possible. Several exemplary embodiments with exemplary signals are illustrated in following FIGS. 5 to 8.

Figure 5:
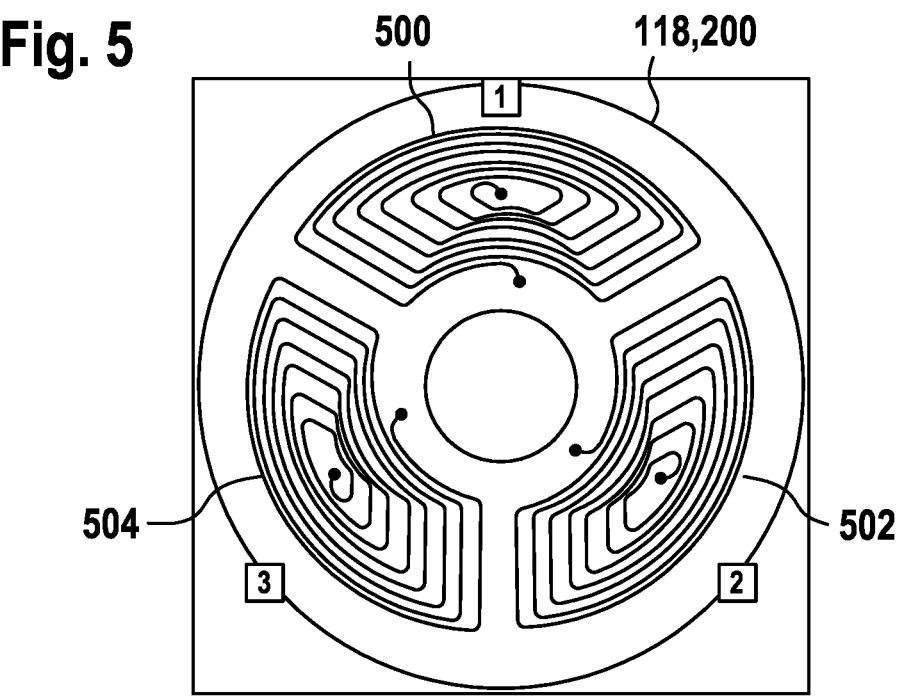
FIG. 5 shows an illustration of a coil unit having three coils according to one exemplary embodiment.

FIG. 5 shows an illustration of a coil unit 118 comprising three coils 500, 502, 504 according to one exemplary embodiment. The coil unit 118 is designed as a circular-ring-shaped printed circuit board 200. The coils 500, 502, 504 are formed on one side of the printed circuit board 200 as planar coils each made of a conductor track arranged in a spiral. Each coil has the shape of a circular ring segment and covers approximately 120°.

Figure 6:
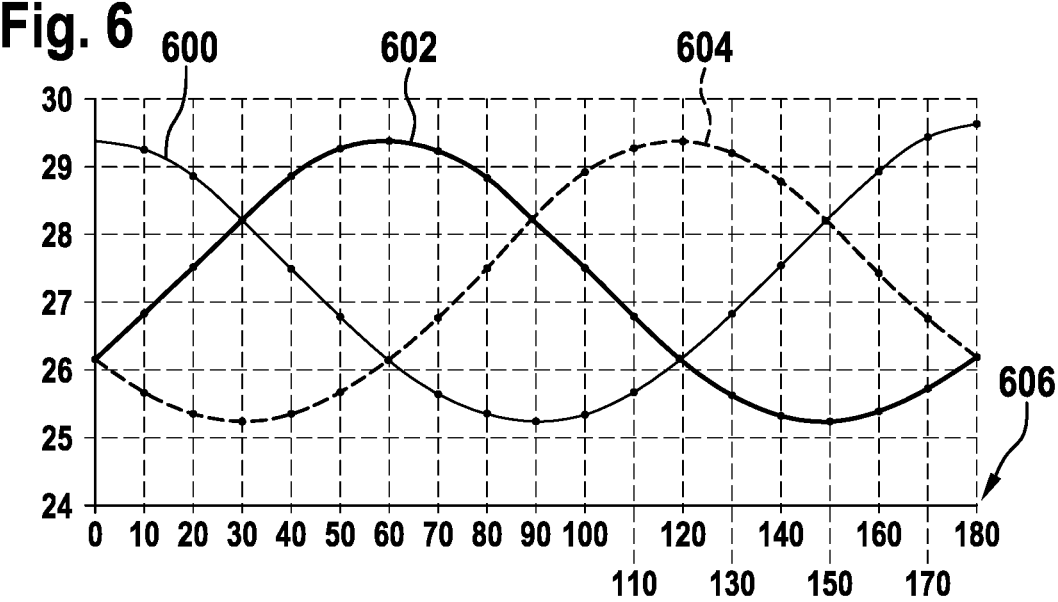
FIG. 6 shows an illustration of rotational angle signals of a three-coil coil unit according to one exemplary embodiment.
Figure 6:
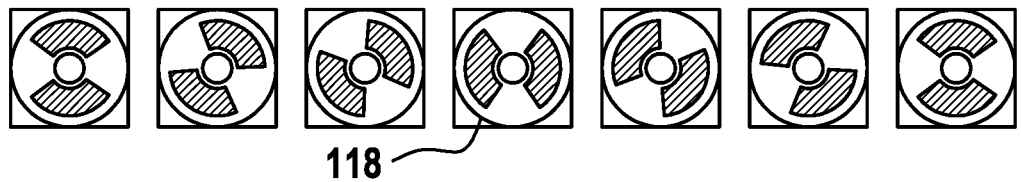

FIG. 6 shows an illustration of resonance curves 600, 602, 604 of a three-coil coil unit according to one exemplary embodiment. The coil unit substantially corresponds to the coil unit in FIG. 5. The signals 600, 602, 604 represent the resonance frequencies of three resonant circuits as a function of a rotational angle 606 of an interference surface unit 118. The three resonant circuits each substantially correspond in this case to a resonant circuit as illustrated in FIG. 4. The coils of the resonant circuits substantially correspond to the coils in FIG. 5. The resonance curves 600, 602, 604 are plotted in a diagram which has the rotational angle of the interference surface unit 118 plotted in degrees over half a resolution on the abscissa. The resonance frequency is plotted on the ordinate. The resonance curves 600, 602, 604 are sinusoidal curves having a phase shift of 60° in relation to one another.

In one exemplary embodiment, three coils 500, 502, 504 are scanned by two targets 118. A coil design consisting of three sensor coils 500, 502, 504 is shown. The coil segments have an opening angle of 100°.

An approximately sinusoidal signal curve 600, 602, 604 can be achieved by overlap with two target elements 118, which have an opening angle of 120°. The three-phase sinusoidal signal 600, 602, 604 can be converted by means of Clarke transformation into a sine/cosine signal. The rotational angle 606 is computed by applying the arctan function. The target 118 is advantageously embodied as a stamped part or as a printed circuit board and is arranged at a distance between 0.5 mm and 1.5 mm in relation to the sensor printed circuit board 200. The uniqueness and/or a measurement range of the assembly of 120° can be arbitrarily expanded by counting the periods, and therefore angles greater than 120° are also measurable.

Figure 7:
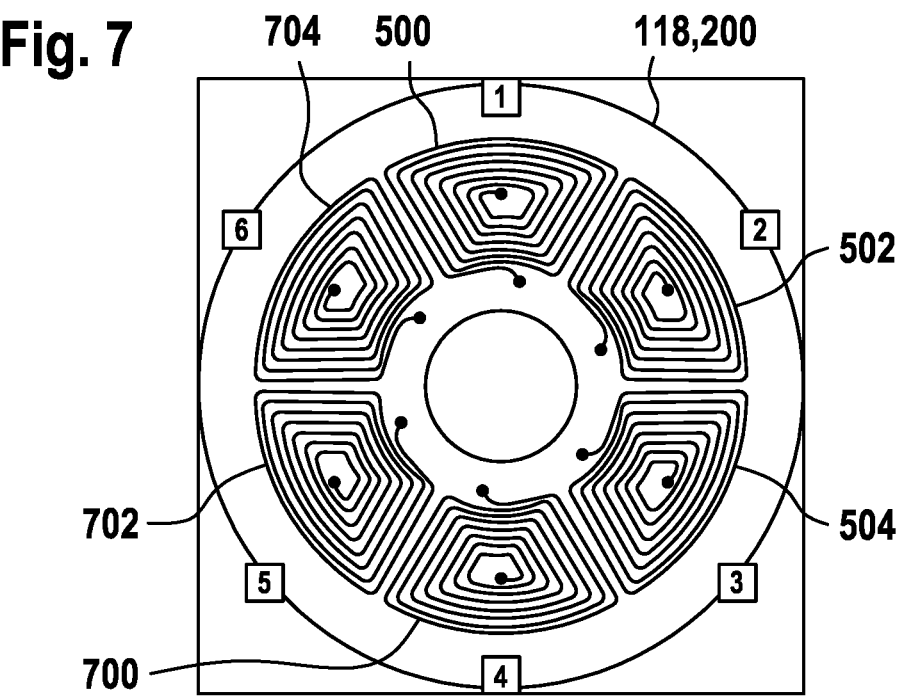
FIG. 7 shows an illustration of a coil unit having six coils according to one exemplary embodiment.

FIG. 7 shows an illustration of a coil unit 118 having six coils 500, 502, 504, 700, 702, 704 according to one exemplary embodiment. The coil unit 118 substantially corresponds to the coil unit in FIG. 6. In contrast thereto, a circular-ring-segment-shaped flat coil covers an angle of 60°.

Figure 8:
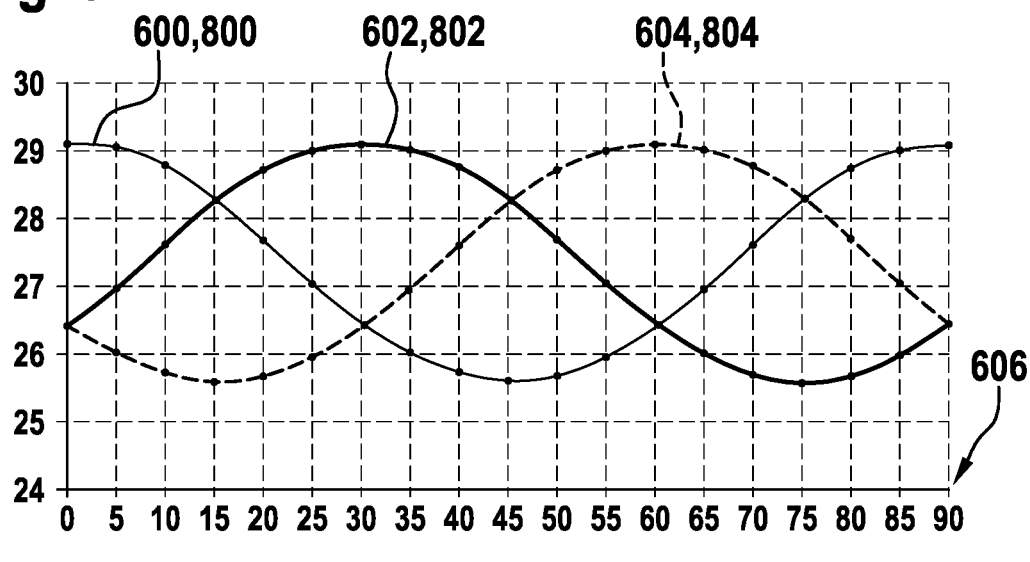
FIG. 8 shows an illustration of rotational angle signals of a six-coil coil unit according to one exemplary embodiment.
Figure 8:
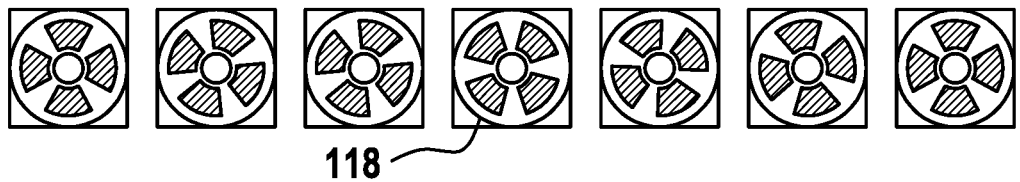

FIG. 8 shows an illustration of resonance curves 600, 602, 604, 800, 802, 804 of a six-coil coil unit according to one exemplary embodiment. The illustration substantially corresponds to the illustration in FIG. 6. In contrast thereto, the rotational angle 606 is plotted over one-fourth revolution here on the abscissa. The first resonance curve 600 and the fourth resonance curve 800 correspond. The second resonance curve 602 and the fifth resonance curve 802 correspond and have a phase shift of 30° in relation to the first resonance curve 600 and the fourth resonance curve 800. The third resonance curve 604 and the sixth resonance curve 804 correspond and have a phase shift of 30° in relation to the second resonance curve 602 and the fifth resonance curve 802.

In one exemplary embodiment, six coils 500, 502, 504, 700, 702, 704 are scanned by four targets 118. A coil design consisting of six sensor coils 500, 502, 504, 700, 702, 704 is shown. The coil segments have an opening angle of 50°. An approximately sinusoidal signal curve 600, 602, 604, 800, 802, 804 can be achieved by overlap with four target elements 118, which have an opening angle of 60°. The three-phase sinusoidal signal 600, 602, 604, 800, 802, 804 can be converted by means of Clarke transformation into a sine/cosine signal. The rotational angle is computed by applying the arctan function.

The signals of the first and the fourth coil, the second and the fifth coil, and the third and the sixth coil are ideally identical. It is possible to use this identity for redundancy purposes. The first, third, and fifth coils and the second, fourth, and sixth coils thus ideally form an independent system. Furthermore, opposing coils can also be connected in series. In general, other coil and target geometries and the combinations thereof are also conceivable.

It is also possible to adapt the coils to different frequencies and to improve the EMC properties in this manner.

FIG. 9 shows a flow chart of a method 900 for operating a determination device according to one exemplary embodiment. The method 900 can be executed on a determination device as shown in FIG. 1, for example. The method is suitable for the purpose of operating a determination device for determining a dose of a dose metering device. The method 900 has a step 902 of reading in and a step 904 of establishing. In step 902 of reading in, a rotational angle signal of an eddy-current-based rotational angle sensor, which is coupled to a rotatable dosing knob of the dose metering device, of the determination device is read in. The rotational angle signal images a rotational angle of the dosing knob representing the dose. In step 904 of establishing, a value of the dose is established using the rotational angle signal.

If an exemplary embodiment comprises an "and/or" linkage between a first feature and a second feature, this is thus to be read to mean that the exemplary embodiment has both the first feature and also the second feature according to one embodiment and has either only the first feature or only the second feature according to a further embodiment.

The invention claimed is:

1. A determination device for determining a value representing a dose of a dose metering device, the determination device comprising:
   an eddy-current-based rotational angle sensor configured to be coupled to a rotatable dosing knob of the dose metering device, and further configured to image a rotational angle of the dosing knob representing the dose in a rotational angle signal; and
   an analysis device configured to establish the value of the dose using the rotational angle signal.

2. The determination device as claimed in claim 1, further comprising:
   a coil unit and an electrically conductive interference surface unit included in the rotational angle sensor, the interference surface unit spaced apart in relation to the coil unit and arranged to be rotatable.

3. The determination device as claimed in claim 2, further comprising:
   a number of coils included in the coil unit, the number of coils being different from a number of interference surfaces of the interference surface unit.

4. The determination device as claimed in claim 3, wherein the number of the coils is greater than the number of the interference surfaces of the interference surface unit.

5. The determination device as claimed in claim 3, wherein:
   the coils of the coil unit are formed as conductor tracks on a printed circuit board.

6. The determination device as claimed in claim 5, wherein the conductor tracks are aligned orthogonally to an axis of rotation of the dosing knob.

7. The determination device as claimed in claim 2, further comprising:
   at least two interference surfaces included in the interference surface unit and/or at least three coils included in the coil unit.

8. The determination device as claimed in claim 1, further comprising:
   a display device configured to display the value of the dose or a parameter representing the value of the dose.

9. The determination device as claimed in claim 1, further comprising:
   a communication device configured to provide the value of the dose or a parameter representing the value of the dose.

10. The determination device as claimed in claim 1, wherein:
    the rotational angle sensor is further configured to provide a dispensing signal upon dispensing of the dose.

11. A dose metering device comprising:
    a dosing knob configured to set a dose amount, wherein the dose amount is settable via a rotational angle of the dosing knob; and
    a determination device configured to determine a value representing the dose amount of the dose metering device, the determination device including:
      an eddy-current-based rotational angle sensor configured to be coupled to the dosing knob and further configured to image a rotational angle of the dosing knob representing the dose amount in a rotational angle signal; and
      an analysis device configured to establish the value of the dose amount using the rotational angle signal,
    wherein the rotational angle sensor is coupled to the dosing knob to determine the rotational angle.

12. The dose metering device as claimed in claim 11, wherein:
    the analysis device is arranged in the dosing knob.

13. A method for operating a determination device to determine a dose of a dose metering device, the method comprising:
    reading a rotational angle signal of an eddy-current-based rotational angle sensor of the determination device, the eddy-current-based rotational angle sensor coupled to a rotatable dosing knob of the dose metering device;
    imaging a rotational angle of the dosing knob representing the dose using the rotational angle signal; and
    establishing a value of the dose using the rotational angle signal.

14. The method as claimed in claim 13, further comprising:
    applying an AC voltage to the rotational angle sensor to establish the rotational angle signal when reading the rotational angle signal.

15. The method as claimed in claim 13, further comprising:
    establishing a collective value using values representing a plurality of doses when establishing the value of the dose.

16. The method as claimed in claim 13, wherein a computer program is configured to execute the method.

17. The method as claimed in claim 16, wherein the computer program is stored on a machine-readable storage medium.

\* \* \* \* \*